(12) United States Patent
Stucchi et al.

(10) Patent No.: US 8,247,546 B2
(45) Date of Patent: Aug. 21, 2012

(54) DERIVATIVES OF ACID POLYSACCHARIDES

(75) Inventors: Luca Stucchi, Udine (IT); Marco Bosco, Gorzia (IT); Rita Gianni, Trieste (IT); Fabrizio Picotti, Udine (IT)

(73) Assignee: Siega S.R.L., Trieste (IT)

( * ) Notice: Subject to any disclaimer, the term of this patent is extended or adjusted under 35 U.S.C. 154(b) by 304 days.

(21) Appl. No.: 12/521,307

(22) PCT Filed: Dec. 18, 2007

(86) PCT No.: PCT/IB2007/003973
§ 371 (c)(1),
(2), (4) Date: Jun. 26, 2009

(87) PCT Pub. No.: WO2008/081255
PCT Pub. Date: Jul. 10, 2008

(65) Prior Publication Data
US 2010/0292459 A1   Nov. 18, 2010

(30) Foreign Application Priority Data
Dec. 29, 2006   (EP) ................................. 06425874

(51) Int. Cl.
*C08B 37/02*  (2006.01)
*C08B 37/00*  (2006.01)
*C07H 5/04*   (2006.01)
*C07H 5/06*   (2006.01)

(52) U.S. Cl. ............. 536/55.1; 536/51; 536/52; 536/53; 536/55.3

(58) Field of Classification Search ................. None
See application file for complete search history.

(56) References Cited

U.S. PATENT DOCUMENTS

| | | | |
|---|---|---|---|
| 2,589,226 A | | 3/1952 | Carson |
| 3,758,577 A | * | 9/1973 | Dinbergs .................. 564/4 |
| 4,152,170 A | | 5/1979 | Nagase et al. |
| 4,675,393 A | * | 6/1987 | Coxon ................. 536/18.6 |
| 5,221,739 A | * | 6/1993 | Wildfeuer ............. 540/230 |
| 6,410,044 B1 | | 6/2002 | Chudzik et al. |
| 6,552,184 B1 | * | 4/2003 | Pallado et al. .......... 536/55.3 |

FOREIGN PATENT DOCUMENTS

| | | |
|---|---|---|
| EP | 0341745 A1 * | 11/1989 |
| FR | 2752843 A1 | 3/1998 |
| WO | WO 2005092929 A1 * | 10/2005 |

* cited by examiner

*Primary Examiner* — Layla Bland
(74) *Attorney, Agent, or Firm* — Porzio, Bromberg & Newman, P.C.

(57) ABSTRACT

Acid polysaccharides characterized by the concomitant presence of partial esters with non-polysaccharide carboxylic acids and esters between the acid groups of the initial polysaccharide and the alcohol groups of the repetitive units, with the formation of crosslinking among the polysaccharide chains.

15 Claims, 4 Drawing Sheets

US 8,247,546 B2

DERIVATIVES OF ACID POLYSACCHARIDES

CROSS-REFERENCE TO RELATED APPLICATION

This is a National Stage of International Application PCT/IB2007/003973, filed 18 Dec. 2007, which claims the benefit of Application No. 06425874.2, filed in Europe on 29 Dec. 2006, the disclosures of which Applications are incorporated by reference herein.

This invention relates to acid autocrosslinked polysaccharides characterised by the concomitant presence of esters with non-polysaccharide carboxylic acids and esters between the acid groups of the same polysaccharide and the alcoholic groups of the repetitive units.

PRIOR ART

In view of their chemico-physical and biological-biochemical characteristics, carboxylated polysaccharides, whether natural or semisynthetic, constitute raw materials of considerable interest for a wide variety of applications in the pharmaceutical and cosmetic industries. Some of them, such as hyaluronic acid (HA), are particularly valued for their high level of biotolerability and hydratability. The choice of material is often connected with cost aspects based on the value and importance of the final application.

Many structural changes have been made to these polysaccharides in recent years to optimise their characteristics and make them as suitable as possible for the desired applications. These changes usually involve the alcohol groups of the repetitive units, the carboxyl groups and, if present, the amino groups.

The prior art as a whole describes two specific structural solutions:

1) simple monoesterification of the alcoholic hydroxyls of the repetitive polysaccharide units, regardless of their nature and origin, with organic acids, without intermolecular crosslinking;

2) formation of autocrosslinking esters between the hydroxyls of the repetitive polysaccharide units and the carboxyls present in the polysaccharide.

EP 0941253 describes the synthesis of HA derivatives with butyric anhydride in a basic environment, to obtain a product not crosslinked, having esterified hydroxy groups and which does not undergo any significant modification of its viscoelastic properties in aqueous solution. The process involves the use of the quaternary ammonium salt of HA and dimethylformamide (DMF) as aprotic solvent.

In EP 341745, starting from HA or from HA wherein the carboxyls are partially esterified with alcohols of various types, including biologically active alcohols, the carboxyl function of HA (or of its ester derivatives, defined as "external") is involved in the formation of intra- or intermolecular esters with the alcoholic hydroxyls of the repetitive units, with consequent crosslinking (defined as "autocrosslinking") and inducement of viscoelastic characteristics which did not exist in the starting polysaccharide. EP 341745 teaches that autocrosslinking is obtained by "activating" the carboxyl by substituting the —OH group with an electron-attractor group X that allows the carbonyl carbon to be attached by a nucleophil (such as the —OH group of the monosaccharide units), with simultaneous detachment of X. The reagents described which are able to activate the carboxyl are the typical, well-known reagents that supply activated esters in peptide synthesis, such as water-soluble carbodiimides, carbonyldiimidazole, carbonyltriazole, N-hydroxysuccinimide, p-nitrophenol, p-nitrophenyltrifluoracetate, and salts of 2-halogen-N-alkylpyridine [T. Mukaiyama, Ang. Chem., 10 (18) 1979, 707-808]; the reaction is catalysed with triethylamine (TEA). The starting carboxylated polysaccharides are salified as tetrabutylammonium (TBA) salts soluble in aprotic solvents, such as dimethyl sulphoxide (DMSO), to obtain a single reaction phase. The same patent also claims the use of sodium salts in the same aprotic organic solvents to conduct the same reaction. However, this conflicts with the knowledge of the skilled person and with the example given in the patent, as it is well known that this salt is not soluble in solvents such as DMF or DMSO. Since the modulation of the chemico-physical, rheological and biological characteristics (in the broadest sense) of products based on carboxylated polysaccharides is crucial for the purpose of the desired final application(s), and the problem does not appear to have been solved to date, at least in the field of this invention, there is a strongly-felt need for products with adjustable, reproducible, advantageous characteristics, especially their rheological properties in terms of the viscosity of solutions at different concentrations, viscoelasticity and biotolerability.

DESCRIPTION OF THE INVENTION

Figure 1:
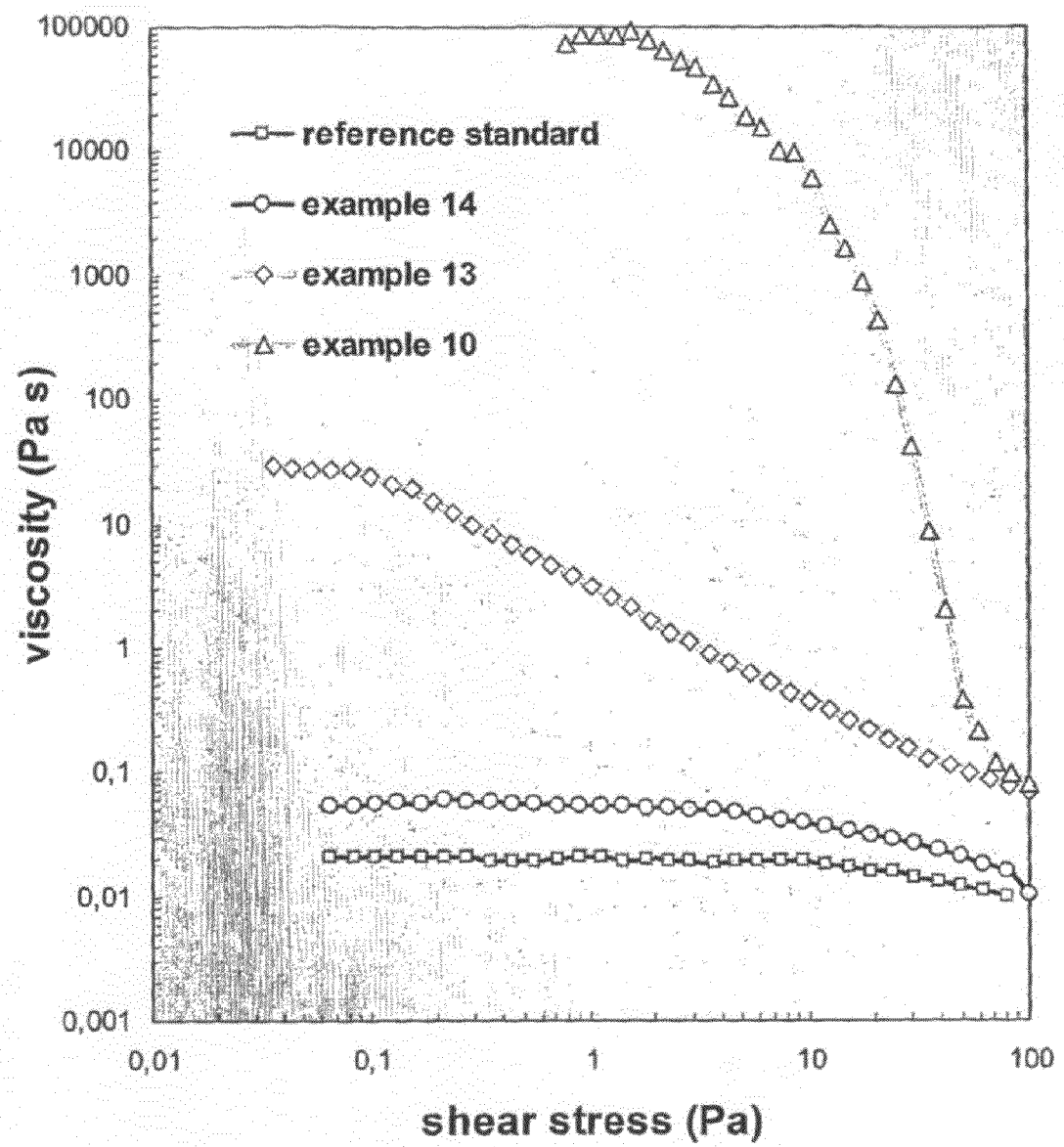
FIG. 1 is a graph of a flow curve with zero-shear viscosity ranges vs shear stress with different cross-linking degrees according to examples 10, 13 and 14 and at the reference standard.

It has now been found that the above-mentioned objectives can be achieved with autocrosslinked polysaccharide derivatives, characterised by the concomitant presence of esters with non-polysaccharide carboxylic acids and esters between the acid groups of the same polysaccharide and the alcoholic groups of their repetitive units. Compounds simultaneously exhibiting the features of esterification to the hydroxyl groups and autocrosslinking have not been disclosed in the prior art.

The invention relates to natural or semisynthetic derivatives of acid polysaccharides wherein the alcoholic groups of the repetitive units occur, more or less extensively, in the form of esters with non-polysaccharide carboxylic acids, and the uronic acid groups are esterified, to a different extent, with other free alcoholic groups present in the polysaccharide chains. This latter type of bond induces autocrosslinking of the polysaccharide, thus influencing the viscoelastic behaviour of the end products; a suitable choice of acyl residue used to esterify the alcoholic hydroxyls enables other chemico-physical properties, such as hydrophilia/lipophilia and viscosity, to be modulated. The degree of autocrosslinking, which is adjustable and reproducible, influences the characteristics of the final products (rigid gels, weak gels, products with increased viscosity). In view of their chemico-physical and rheological characteristics, the derivatives according to the invention can be used as constituents of medical devices of various grades (I, II and III), such as injectable dermal fillers, post surgical antiadherence materials, devices for healing sores and wounds, etc., in slow-release galenical formulations, etc.).

The rheological tests demonstrate that the derivatives according to the invention possess rheological properties characterised by viscoelastic behaviour which can be modulated according to the degree of autocrosslinking of the system, which ranges from a solution to that characteristic of a strong gel. It was found that the viscosity at low shear rates and the resistance to the force applied could be easily modulated. Finally, it was found that the polymer mixtures of the invention have a good ability to recover their viscoelastic properties after a rheological history of imposed stresses (pseudoplastic properties).

The invention also relates to the process for the preparation of these derivatives comprising the reaction, in homogenous phase in the protic, polar solvent formamide, of the salt of a monovalent inorganic cation, such as sodium or potassium, of the selected carboxylated polysaccharide with an anhydride of an alkylcarboxylic acid, such as acetic, butyric, isobutyric, valeric, isovaleric or crotonic anhydride, etc., in the presence of a basic catalyst containing an atom of trisubstituted nitrogen, or an inorganic base such sodium or potassium salt of phosphoric acid or a salt of an organic acid with sodium or potassium. The range of the hydroxyl residues involved in ester bonds with the acyl residue deriving from the anhydride is between 0.01 and 0.9×N, where N is the number of hydroxyls in the repetitive unit. Furthermore, the formate ester formed by the formamide hydrolysis in the particular reaction environment may not be higher than 0.2.

The starting polysaccharides can be in native form or differently modified according to the chemical functions present.

The advantage of direct use of an inorganic cation salt is obvious because, as described below, it eliminates the need for preliminary transformation of the polysaccharide into the salt of an organic base (such as TBA) soluble in aprotic solvents such as DMF, DMSO, N-methylpyrrolidone, etc., a lengthy, expensive operation which involves the risk of depolymerisation.

All the tests confirm the modulability and reproducibility of the process according to the invention. Using said process, it is possible to choose which rheological aspect should be given priority in order to obtain products that present a simple increase in their viscosity in solution (low degree of autocrosslinking and different degree of esterification) or derivatives with variable viscoelastic properties ranging from weak gels to strong gels.

Acid polysaccharides, either in acid form or in the form of their inorganic salts, according to the invention are glycosaminoglycan selected from: hyaluronan, chondroitin sulphate, heparan sulphate, dermatan sulphate, keratan sulphate. Hyaluronic acid is particularly preferred.

The molecular weight of the polysaccharides according to the invention can vary within a wide range, e.g. between $10^3$ and $10^7$ Daltons.

The products according to the invention can be used as moisturising (dermo-) cosmetic agents, medical devices, intra-articular viscosupplementation agents, post surgical anti-adherence filling materials, and materials for covering wounds or sores.

The products according to the invention can also be advantageously used as a carrier for the controlled release or absorption of active drugs.

The following examples illustrate the invention in greater detail.

EXAMPLES

The $^1$H NMR analyses are conducted in $D_2O$ with a Bruker Advance 400 spectrometer equipped with a 5 mm multinuclear probe with gradient z, at 300° K. The analyses also use diffusion-ordered experiments (DOSY: Diffusion Ordered Spectroscopy).

The rheological tests were performed with a Rheostress Haake RS150 controlled-stress rotational rheometer.

The determination of the percentage of ester groups of the polysaccharide alcoholic hydroxyls with the various non-polysaccharide carboxylic acids (DE) and with the polysaccharide carboxyls (AUC) was expressed as the molar ratio between the moles of ester and polysaccharide by means of $^1$H NMR spectroscopic analysis.

A sample of esterified, cross-linked polysaccharide swollen in formamide containing excess propylamine is left under magnetic stirring at ambient temperature for 16 hours. The polysaccharide is recovered by precipitation in acetone, washed with acetone and dried. The solid is analysed by $^1$H NMR. The acylation reaction of the amine with carboxyl esters (Michael B. Smith and Jerry March—*March's Advanced Organic Chemistry*, 5th ed., Wiley Interscience, page 510) is exploited to determine the esters previously used in the crosslinking; this methodology is selective, because the bland conditions used only involve unstable esters. The esters to the hydroxyls are analysed, again with $^1$H NMR, exploiting the different resonance of the methyls and methylenes of the acyl residues bonded to the hydroxyls compared with the other polymer signals. These analysis are performed after addition of few microliters of a NaOD solution directly inside the NMR tube containing the swollen gel in $D_2O$ thus inducing full hydrolysis of both the crosslink esters and the esters with the non-saccharide acids.

The following examples describe the details of the synthesis of some acid autocrosslinked polysaccharides according to the invention.

Example 1

Synthesis of Cross-Linked Hyaluronic Acid, Sodium Salt, Acetate Ester; Degree of Autocrosslinking (AUC): 0.07; Degree of Esterification (DE): 0.19 (Acetate), 0.12 (Formate)

1.00 g of hyaluronic acid in the form of sodium salt, with a molecular weight of approx. 300 kD, equal to 2.49 mmols of monomer units, was dissolved in 33 mL of formamide at 95° C., under nitrogen flow, with mechanical stirring. The solution was then cooled to room temperature, and 352 µL of acetic anhydride (3.73 mmols) and 312 µL of triethylamine (2.24 mmols) were added. After 16 hours reaction, a further 521 µL of triethylamine (3.74 mmols) was added, and the system was left to stir for another 6 hours.

The gel was then transferred, slowly and under constant agitation, into 100 mL of an 0.2 M solution of NaCl, transferred to a dialysis membrane (cut-off 12,000 D) and dialysed, firstly against 0.2 M NaCl and secondly against demineralised water. Finally, it was frozen and freeze-dried.

0.94 g of white lyophilisate was obtained.

The product, analysed in accordance with the method described above, presented AUC: 0.07; DE: 0.19 (acetate), 0.12 (formate).

Example 2

Synthesis of Cross-Linked Hyaluronic Acid, Sodium Salt, Acetate Ester; Degree of Autocrosslinking (AUC): 0.05; Degree of Esterification (DE): 0.16 (Acetate), 0.01 (Formate)

1.00 g of hyaluronic acid in the form of sodium salt, with a molecular weight of approx. 300 kD, equal to 2.49 mmols of monomer units, was dissolved in 33 mL of formamide at 80° C., under nitrogen flow, with mechanical agitation. The solution was then cooled to ambient temperature, and 235 μL of acetic anhydride (2.49 mmols) and 311 μL of triethylamine (2.23 mmols) were added. After 16 hours, a further 320 μL of triethylamine (2.29 mmols) was added, and the system was left to stir for further 6 hours.

The gel was then transferred, slowly and under constant agitation, into 70 mL of an 0.2 M solution of NaCl, and neutralised with $KH_2PO_4$. After approx. 16 hours' agitation, the system was transferred to a dialysis membrane (cut-off 12000 D) and dialysed, firstly against 0.2 M NaCl and secondly against demineralised water. Finally, it was frozen and freeze-dried.

0.9 g of white lyophilisate was obtained.

The product, analysed in accordance with the method described above, presented AUC: 0.05; DE: 0.16 (acetate), 0.01 (formate).

Example 3

Synthesis of Cross-Linked Hyaluronic Acid Acetate Sodium Salt, Degree of Autocrosslinking (AUC): 0.05; Degree of Esterification (DE): 0.15 (Acetate), 0.05 (Formate)

1.00 g of hyaluronic acid in the form of sodium salt, with a molecular weight of approx. 300 kD, equal to 2.49 mmols of monomer units, was dissolved in 33 mL of formamide at 95° C., under nitrogen flow, with mechanical agitation. The solution was then cooled to ambient temperature, and 235 μL of acetic anhydride (2.49 mmols) and 277 μL of triethylamine (1.99 mmols) were added. After 16 hours' reaction, a further 417 μL of triethylamine (3.00 mmols) was added, and the system was left to stir for another 6 hours.

The gel was then transferred, slowly and under constant agitation, into 70 mL of an 0.2 M solution of NaCl, and then to a dialysis membrane (cut-off 12000 D) and dialysed, firstly against 0.2 M NaCl and secondly against demineralised water. Finally, it was frozen and freeze-dried.

0.98 g of white lyophilisate was obtained.

The product, analysed in accordance with the method described above, presented AUC: 0.05; DE: 0.15 (acetate), 0.05 (formate).

Example 4

Synthesis of Cross-Linked Hyaluronic Acid Acetate Sodium Salt, Degree of Autocrosslinking (AUC): 0.03; Degree of Esterification (DE): 0.12 (Acetate), 0.03 (Formate)

1.02 g of hyaluronic acid in the form of sodium salt, with a molecular weight of approx. 300 kD, equal to 2.54 mmols of monomer units, was dissolved in 33 mL of formamide at 95° C., under nitrogen flow, with mechanical agitation. The solution was then cooled to ambient temperature, and 120 μL of acetic anhydride (1.27 mmols) and 140 μL of triethylamine (1.01 mmols) were added. After 22 hours a further 140 μL of triethylamine (1.01 mmols) was added, and the gelatinous mass obtained was left to stir for further 6 hours.

The reaction mixture was then transferred into 100 mL of an 0.2 M solution of NaCl, poured into a dialysis membrane (cut-off 12,000 D) and dialysed, firstly against an 0.2 M solution of NaCl and secondly against demineralised water. Finally, the sample was frozen and freeze-dried, and 1.00 g of white lyophilisate was obtained.

The product, analysed in accordance with the method described above, presented AUC: 0.03; DE: 0.12 (acetate), 0.03 (formate).

Example 5

Synthesis of Cross-Linked Hyaluronic Acid Acetate Sodium Salt, Degree of Autocrosslinking (AUC): 0.01; Degree of Esterification (DE): 0.05 (Acetate), 0.01 (Formate)

1.00 g of hyaluronic acid in the form of sodium salt, with a molecular weight of approx. 300 kD, equal to 2.49 mmols of monomer units, was dissolved in 33 mL of formamide at 95° C., under nitrogen flow, with mechanical agitation. The solution was then cooled to ambient temperature, and 82 μL of acetic anhydride (0.87 mmols) and 87 μL of triethylamine (0.63 mmols) were added. After 19 hours a further 348 μL of triethylamine (2.52 mmols) was added, and the gelatinous mass obtained was left to stir for further 6 hours.

The reaction mixture was then transferred into 100 mL of demineralised water, poured into a dialysis membrane (cut-off 12000 D) and dialysed, firstly against an 0.2 M solution of NaCl and secondly against demineralised water. Finally, the sample was frozen and freeze-dried, and 0.89 g of white lyophilisate was obtained.

The product, analysed in accordance with the method described above, presented AUC: 0.01; DE: 0.05 (acetate), 0.01 (formate).

Example 6

Synthesis of Cross-Linked Hyaluronic Acid Acetate Sodium Salt, Degree of Autocrosslinking (AUC): 0.03; Degree of Esterification (DE): 0.08 (Acetate), 0.18 (Formate)

2.00 g of hyaluronic acid in the form of sodium salt, with a molecular weight of approx. 300 kD, equal to 4.99 mmols of monomer units, was solubilised in 67 mL of formamide at 80° C., under nitrogen flow, with mechanical agitation. The solution was then cooled to ambient temperature, and 710 μL of acetic anhydride (7.52 mmols) and 970 μL of triethylamine (6.97 mmols) were added.

After 2 hours 30 minutes the gel was transferred into 350 mL of an 0.2 M solution of NaCl, and the mixture was transferred to a dialysis membrane (cut-off 12000 D) and dialysed, firstly against 0.2 M NaCl and then exhaustively against demineralised water. Finally, the sample was frozen and freeze-dried, and 2.10 g of white lyophilisate was obtained.

The product, analysed in accordance with the method described above, presented AUC: 0.03; DE: 0.08. (acetate), 0.18 (formate).

Example 7

Synthesis of Cross-Linked Hyaluronic Acid Acetate Sodium Salt, Degree of Autocrosslinking (AUC): 0.03; Degree of Esterification (DE): 0.23 (Acetate), 0.19 (Formate)

1.01 g of hyaluronic acid in the form of sodium salt, with a molecular weight of approx. 300 kD, equal to 2.49 mmols of monomer units, was dissolved in 33 mL of formamide at 95° C., under nitrogen flow, with mechanical agitation. The solution was then cooled to ambient temperature, and 240 μL of acetic anhydride (2.54 mmols) and a solution of 0.28 g of dimethylaminopyridine (2.29 mmols), dissolved in 2 mL of formamide, were added. After 19 hours, a further 0.56 μL of dimethylaminopyridine (4.58 mmols), dissolved in 4 mL of formamide, was added, and the system was stirred for further 5 hours.

The gel was then transferred, slowly and under constant agitation, into 150 mL of an 0.2 M solution of NaCl, and neutralised with $KH_2PO_4$. It was then transferred to a dialysis membrane (cut-off 12000 D) and dialysed, firstly against 0.2 M NaCl and secondly against demineralised water. Finally, it was frozen and freeze-dried.

1.09 g of white lyophilisate was obtained.

The product, analysed in accordance with the method described above, presented AUC: 0.03; DE: 0.23 (acetate), 0.19 (formate).

Example 8

Synthesis of Cross-Linked Hyaluronic Acid Propionate Sodium Salt, Degree of Autocrosslinking (AUC): 0.05; Degree of Esterification (DE): 0.06 (Propionate), 0.07 (Formate)

1.02 g of hyaluronic acid in the form of sodium salt, with a molecular weight of approx. 300 kD, equal to 2.54 mmols of monomer units, was dissolved in 33 mL of formamide at 95° C., under nitrogen flow, with mechanical agitation. The solution was then cooled to ambient temperature, and 330 μL of propionic anhydride (2.57 mmols) and 320 μL of triethylamine (2.30 mmols) were added.

The reaction mixture was then maintained under agitation for approximately 3 hours, and a further 320 μL of triethylamine (2.30 mmols) was added. After 2 hours, the gel was transferred into 100 mL of demineralised water and neutralised with $KH_2PO_4$. It was then transferred to a dialysis membrane (cut-off 12000 D) and dialysed, firstly against 0.2 M NaCl and secondly against demineralised water.

Finally, the sample was frozen and freeze-dried, and 0.96 g of white lyophilisate was obtained.

The product, analysed in accordance with the method described above, presented AUC: 0.05; DE: 0.06 (propionate), 0.07 (formate).

Example 9

Synthesis of Cross-Linked Hyaluronic Acid Butyrate Sodium Salt, Degree of Autocrosslinking (AUC): 0.06; Degree of Esterification (DE): 0.18 (Butyrate), 0.08 (Formate)

1.00 g of hyaluronic acid in the form of sodium salt, with a molecular weight of approx. 300 kD, equal to 2.52 mmols of monomer units, was dissolved in 33 mL of formamide at 95° C., under nitrogen flow, with mechanical agitation. The solution was then cooled to ambient temperature, and 610 μL of butyric anhydride (3.73 mmols) and 310 μL of triethylamine (2.23 mmols) were added.

The reaction mixture was then maintained under agitation for approximately 20 hours, and a further 550 μL of triethylamine (3.95 mmols) was added. After 6 hours, the gel was transferred into 150 mL of ultrapure water, transferred to a dialysis membrane (cut-off 12000 D) and dialysed, firstly against 0.2 M NaCl and secondly against ultrapure water.

Finally, the sample was frozen and freeze-dried, and 0.95 g of white lyophilisate was obtained.

The product, analysed in accordance with the method described above, presented AUC: 0.06; DE: 0.18 (butyrate), 0.08 (formate).

Example 10

Synthesis of Cross-Linked Hyaluronic Acid Butyrate Sodium Salt, Degree of Autocrosslinking (AUC): 0.05; Degree of Esterification (DE): 0.15 (Butyrate), 0.15 (Formate)

1.01 g of hyaluronic acid in the form of sodium salt, with a molecular weight of approx. 300 kD, equal to 2.52 mmols of monomer units, was dissolved in 33 mL of formamide at 95° C., under nitrogen flow, with mechanical agitation. The solution was then cooled to ambient temperature, and 490 μL of butyric anhydride (3.00 mmols) and 280 μL of triethylamine (2.01 mmols) were added.

The reaction mixture was then maintained under agitation for approximately 5 hours, and a further 280 μL of triethylamine (2.01 mmols) was added. After 16 hours, the gel was transferred into 150 mL of ultrapure water, transferred to a dialysis membrane (cut-off 12000 D) and dialysed, firstly against 0.2 M NaCl and secondly against ultrapure water.

Finally, the sample was frozen and freeze-dried, and 1.00 g of white lyophilisate was obtained.

The product, analysed in accordance with the method described above, presented AUC: 0.05; DE: 0.15 (butyrate), 0.15 (formate).

Example 11

Synthesis of Cross-Linked Hyaluronic Acid Butyrate Sodium Salt, Degree of Autocrosslinking (AUC): 0.03; Degree of Esterification (DE): 0.08 (Butyrate), 0.02 (Formate)

1.00 g of hyaluronic acid in the form of sodium salt, with a molecular weight of approx. 300 kD, equal to 2.49 mmols of monomer units, was dissolved in 33 mL of formamide at 80° C., under nitrogen flow, with mechanical agitation. The solution was then cooled to ambient temperature, and 360 μL of butyric anhydride (2.20 mmols) and 311 μL of triethylamine (2.23 mmols) were added.

The reaction mixture was then maintained under agitation for approximately 16 hours, and a further 311 μL of triethylamine (2.23 mmols) was added. After 6 hours 30 minutes the gel was transferred into approx. 40 mL of an 0.2 M solution of NaCl, transferred to a dialysis membrane (cut-off 12000 D), and exhaustively dialysed against demineralised water. Finally, the sample was frozen and freeze-dried, and 0.90 g of white lyophilisate was obtained.

The product, analysed in accordance with the method described above, presented AUC: 0.03; DE: 0.08 (butyrate), 0.02 (formate).

Example 12

Synthesis of Cross-Linked Hyaluronic Acid Butyrate Sodium Salt, Degree of Autocrosslinking (AUC): 0.03; Degree of Esterification (DE): 0.10 (Butyrate), 0.08 (Formate)

1.00 g of hyaluronic acid in the form of sodium salt, with a molecular weight of approx. 300 kD, equal to 2.52 mmols of monomer units, was dissolved in 33 mL of formamide at 95° C., under nitrogen flow, with mechanical agitation. The solution was then cooled to ambient temperature, and 244 µL of butyric anhydride (1.49 mmols) and 173 µL of triethylamine (1.24 mmols) were added.

The reaction mixture was then maintained under agitation for approximately 16 hours, and a further 208 µL of triethylamine (1.49 mmols) was added. After 6 hours, the gel was transferred into 100 mL of ultrapure water, transferred to a dialysis membrane (cut-off 12000 D) and dialysed, firstly against 0.2 M NaCl and secondly against ultrapure water.

Finally, the sample was frozen and freeze-dried, and 0.95 g of white lyophilisate was obtained.

The product, analysed in accordance with the method described above, presented AUC: 0.03; DE: 0.1 (butyrate), 0.08 (formate).

Example 13

Synthesis of Cross-Linked Hyaluronic Acid Butyrate Sodium Salt, Degree of Autocrosslinking (AUC): 0.02; Degree of Esterification (DE): 0.06 (Butyrate), 0.05 (Formate)

1.00 g of hyaluronic acid in the form of sodium salt, with a molecular weight of approx. 300 kD, equal to 2.49 mmols of monomer units, was dissolved in 33 mL of formamide at 95° C., under nitrogen flow, with mechanical stirring. The solution was then cooled to ambient temperature, and 210 µL of butyric anhydride (1.28 mmols) and 140 µL of triethylamine (1.0 mmols) were added.

The reaction mixture was then maintained under agitation for 17 hours, and a further 320 µL of triethylamine (3.00 mmols) was added. After 6 hours 30 minutes the gel was transferred into 150 mL of ultrapure water, transferred to a dialysis membrane (cut-off 12000 D) and dialysed, firstly against 0.2 M NaCl and secondly against ultrapure water.

Finally, the sample was frozen and freeze-dried, and 0.99 g of white lyophilisate was obtained.

The product, analysed in accordance with the method described above, presented AUC: 0.02; DE: 0.06 (butyrate), 0.05 (formate).

Example 14

Synthesis of Cross-Linked Hyaluronic Acid Butyrate Sodium Salt, Degree of Autocrosslinking (AUC): 0.01; Degree of Esterification (DE): 0.06 (Butyrate), 0.02 (Formate)

1.01 g of hyaluronic acid in the form of sodium salt, with a molecular weight of approx. 300 kD, equal to 2.52 mmols of monomer units, was dissolved in 33 mL of formamide at 95° C., under nitrogen flow, with mechanical agitation. The solution was then cooled to ambient temperature, and 125 µL of butyric anhydride (0.76 mmols) and 75 µL of triethylamine (0.5 mmols) were added.

The reaction mixture was then maintained under agitation for 18 hours, and a further 740 µL of triethylamine (5.32 mmols) was added. After 6 hours, the system was transferred into 200 mL of demineralised water, neutralised with $KH_2PO_4$, transferred to a dialysis membrane (cut-off 12000 D) and dialysed, firstly against 0.2 M NaCl and secondly against water.

Finally, the sample was frozen and freeze-dried, and 0.82 g of white lyophilisate was obtained.

The product, analysed in accordance with the method described above, presented AUC: 0.01; DE: 0.06 (butyrate), 0.02 (formate).

Example 15

Synthesis of Cross-Linked Butyrate, Acetate and Formate Ester Hyaluronic Acid Sodium Salt; Degree of Autocrosslinking (AUC): 0.03; Degree of Esterification (DE): 0.12 (Butyrate), 0.14 (Acetate), 0.06 (Formate)

1.65 g of hyaluronic acid in the form of sodium salt, injection grade, with a molecular weight of approx. 500 kD, equal to 4.11 mmols of monomer units, was dissolved in 33 mL of formamide at 95° C., under nitrogen flow, with mechanical stirring. The solution was then cooled to room temperature and 670 µL of butyric anhydride (4.1 mmols) were added.

The reaction mixture was then maintained under mechanical stirring for approximately 30 minutes, and 2 ml of a formamide solution containing 1.21 g of potassium acetate (12.3 mmols) were added. After 16 hours, the gel was transferred into 200 mL of ultrapure water, transferred to a dialysis membrane (cut-off 12000 D) and dialysed, firstly against 0.2 M NaCl and secondly against ultrapure water.

All the reaction and purification equipment was confined under a vertical laminar flow cabinet to prevent contamination. The glassware and the water were pyrogen free.

Finally, the sample was frozen and freeze-dried, and 1.60 g of white lyophilisate was obtained.

The product, analysed in accordance with the method described above, presented AUC: 0.03; DE: 0.12 (butyrate), 0.14 (acetate), 0.06 (formate).

Example 16

Synthesis of Cross-Linked Hyaluronic Acid Butyrate Sodium Salt, Degree of Autocrosslinking (AUC): 0.03; Degree of Esterification (DE): 0.55 (Butyrate), 0.15 (Formate)

0.50 g of hyaluronic acid butyrate in the form of sodium salt (degree of butyration, namely moles of butyric groups on moles of polysaccharide, equal to approx. 0.54, MW=439 g/mol, 1.14 mmols) was dissolved in 17 mL of formamide at 60° C., under nitrogen flow and with mechanical agitation. The solution was then cooled to ambient temperature, and 186 µL of butyric anhydride (1.14 mmols) and 143 µL of triethylamine (1.03 mmols) were added.

The reaction mixture was then maintained under agitation for 19 hours, and a further 143 µL of triethylamine (1.03 mmols) was added. After 4½ hours the system was transferred into 100 mL of an 0.2 M solution of NaCl, and neutralised with $KH_2PO_4$. It was then transferred to a dialysis membrane (cut-off 12000 D) and dialysed, firstly against 0.2 M NaCl and secondly against demineralised water.

Finally, the sample was frozen and freeze-dried, and 0.45 g of white lyophilisate was obtained.

The product, analysed in accordance with the method described above, presented AUC: 0.03; DE: 0.55 (butyrate), 0.15 (formate).

Example 17

Synthesis of Cross-Linked Hyaluronic Acid Crotonate Sodium Salt, Degree of Autocrosslinking (AUC): 0.05; Degree of Esterification (DE): 0.08 (Crotonate), 0.10 (Formate)

1.02 g of hyaluronic acid in the form of sodium salt, with a molecular weight of approx. 300 kD, equal to 2.54 mmols of monomer units, was dissolved in 32 mL of formamide at 95° C., under nitrogen flow, with mechanical agitation. The solution was then cooled to ambient temperature, and 380 μL of crotonic anhydride (2.56 mmols) and 320 μL of triethylamine (2.30 mmols) were added.

The reaction mixture was maintained under agitation for 18 hours, and a further 320 μL of triethylamine (2.30 mmols) was added. After 7 hours 30 minutes the gel was transferred into 150 mL of ultrapure water, transferred to a dialysis membrane (cut-off 12000 D) and dialysed, firstly against an aqueous solution of 0.2 M NaCl and secondly against ultrapure water.

Finally, the sample was frozen and recovered by freeze-drying.

0.45 g of white lyophilisate was obtained.

The product, analysed in accordance with the method described above, presented AUC: 0.05; DE: 0.08 (crotonate), 0.10 (formate).

Example 18

Synthesis of Cross-Linked Hyaluronic Acid Isovalerate (or 3-Methyl-Butyrate) Sodium Salt, Degree of Autocrosslinking (AUC): 0.03; Degree of Esterification (DE): 0.08 (Isovalerate), 0.02 (Formate)

0.48 g of hyaluronic acid in the form of sodium salt, with a molecular weight of approx. 300 kD, equal to 1.21 mmols of monomer units, was dissolved in 16 mL of formamide at 95° C., under nitrogen flow, with mechanical agitation. The solution was then cooled to ambient temperature, and 240 μL of isovaleric anhydride (1.20 mmols) and 150 μL of triethylamine (1.08 mmols) were added.

The reaction mixture was maintained under agitation for 16 hours, and a further 167 μL of triethylamine (1.20 mmols) was added. After 6 hours, the gel was transferred into 100 mL of demineralised water and neutralised with $KH_2PO_4$, and 2.5 g of NaCl was added. It was then transferred to a dialysis membrane (cut-off 12000 D) and dialysed against water.

Finally, the sample was frozen and recovered by freeze-drying.

0.89 g of white lyophilisate was obtained.

The product, analysed in accordance with the method described above, presented AUC: 0.03; DE: 0.08 (isovalerate), 0.02 (formate).

Example 19

Preparation of a Syringe Containing 1.5 ml of a 2% Hydrogel Based on Autocrosslinked Polymer as Obtained According to Example 15

30 mg of the liophylised autocrosslinked polymer, as obtained according to Example 15, were weighted in a 2.0 ml syringe and 1.47 g of a water solution containing 0.9% (w/V) sodium chloride were added. All the experimental procedures were conducted under a vertical laminar flow cabinet using pyrogen free materials; the above mentioned physiological solution was prepared using pyrogen free water. The polymer was left to swell for 24 hours at room temperature. Finally the syringe was sterilized by means of a standard thermal cycle ad 121° C. for 16 minutes.

Rheological Characterisation of Esterified and Cross-Linked Derivatives

Rheological studies highlight how polymeric systems examined exhibit a wide variety of rheological behaviours depending on the cross-linking density of the network. Indeed for different system reticulation degree, low shear viscosity differs of many decades, and flow curves dramatically vary from a viscous liquid to an elastic solid profile. Further viscoelastic behaviour ranges from solution-like to strong-gel-like confirming the properties variability of products object of the present invention.

Method and Results

For rheological measurements we used a controlled stress rheometer, a mechanical spectrometer capable of subjecting a sample to either a dynamic (sinusoidal) or steady (linear) shear stress.

A magnetic field generates a torque on the upper mobile measurement sensor, air-bearing supported, that converts in stress applied on the sample. At the same time, the resultant rotational degree and speed of the mobile measurement system are detected by an optical laser system, and thus the strain expended by the sample in response to the shear stress, and the shear rate are estimated.

The rheometer used was a Rheostress Haake RS150, equipped with rough or smooth surfaces sensors useful for all types of measurements in rotation and oscillation, respectively for high or low structured systems. All measurements were done at 25° C., using a specific thermocontroller.

Three types of measurements were done in order to characterize the products according to the invention:
  flow curves: continuous/steady state measurements of viscosity over a wide range of shear rate or shear stress;
  stress and frequency sweep: dynamic measurements (oscillation) for the determination of samples viscoelastic behaviour. In particular stress sweep is done in order to individuate the linear viscoelastic range extension, and thus the critical strain value for the linear/non linear transition. Frequency sweep gives systems' mechanical spectra, that are the storage modulus G' and the loss modulus G" profiles over a wide range of frequency, in the linear viscoelasticity field.
  recovery sweep: to evaluate the viscoelastic properties recovery of a sample undergone a certain rheological history: three measurement cycles are applied, each one composed by oscillatory steps, under constant amplitude and frequency of strain, before and after the application of a constant shear rate (respectively 100 $s^{-1}$, 100 $s^{-1}$, 500 $s^{-1}$ during each cycle)

The tests were conducted on samples swollen in saline at the concentration of 1% w/w.

Figure 2:
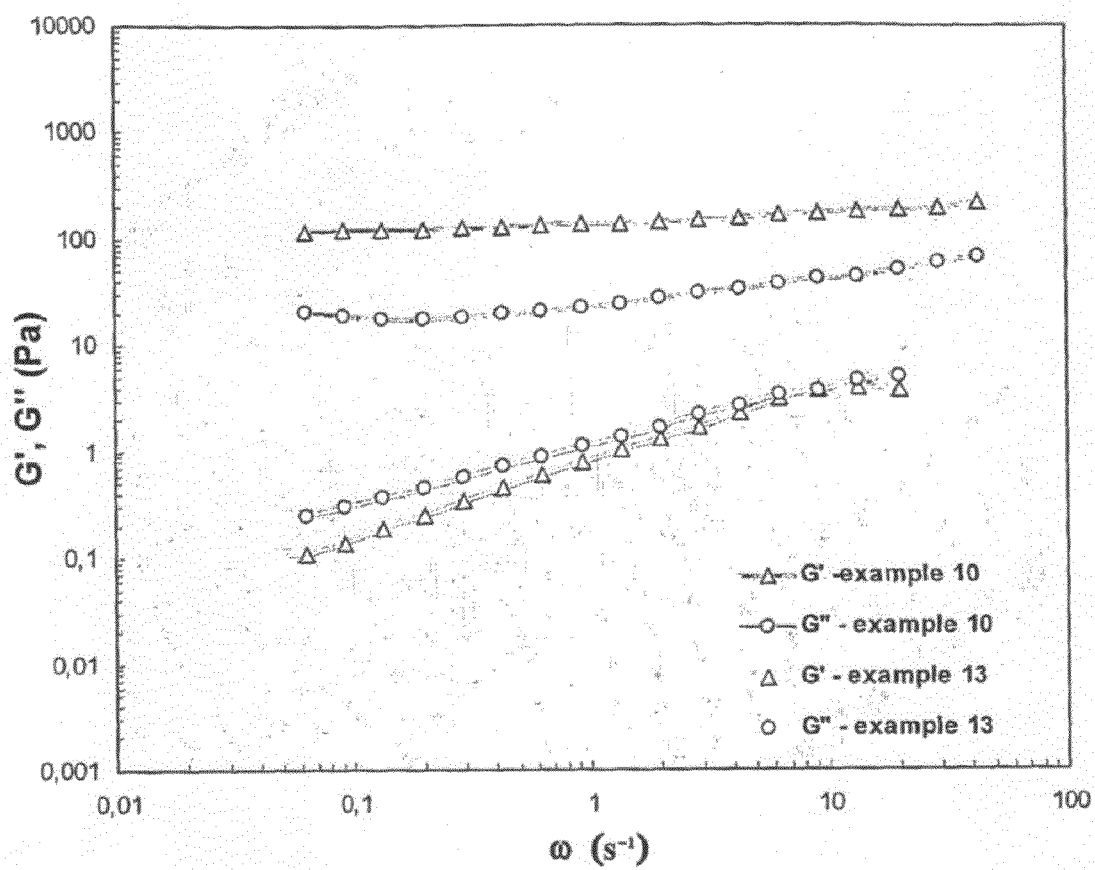
FIG. 2 is a graph of the mechanical flow curves with different cross-linking degrees according to examples 10 and 13.

Examples of flow curves and mechanical spectra, in FIG. 2, of a hyaluronan butyrate esters family in physiological solution 1% w/w, with different cross-linking degree, prepared as described in examples 10, 13, 14 and of the reference standard (HA sodium salt, Mw=300 kDa) are shown in FIGS. 1 and 2, respectively.

Flow Curves—Continuous Steady State Tests

FIG. 1 shows how zero-shear viscosity ranges from 0.01 Pa*s to 100.000 Pa*s by increasing cross-link degree, and how qualitative and quantitative changes occurred on rheological properties over the wide shear stress range. Compounds having a low cross-linking degree behave like solutions while the more crosslinked they are, the more plastic they become. Infact, their profiles range from close to Newtonian to apparently plastic behaviour, characterized by a dramatic viscosity drop of many orders of magnitude over a narrow shear stress range.

Oscillatory Tests

FIG. 2 shows the mechanical spectra of different systems. No mechanical spectra could be recorded for the compounds having the lowest crosslinking degree indicated as reference and example 14, since a linear viscoelasticity field could not be recognised.

As to the other two compounds, it is possible to observe the transition from a solution behaviour to a strong gel profile. Solutions show a viscous modulus (G") higher than the elastic one (G') at low frequencies, while, as the frequency are increased, a module cross-over that takes. Strong gels show a storage modulus higher than the viscous one over the whole experimental range of frequencies. The more structured the systems are, the higher the module values are.

Recovery Tests

Figure 3A:
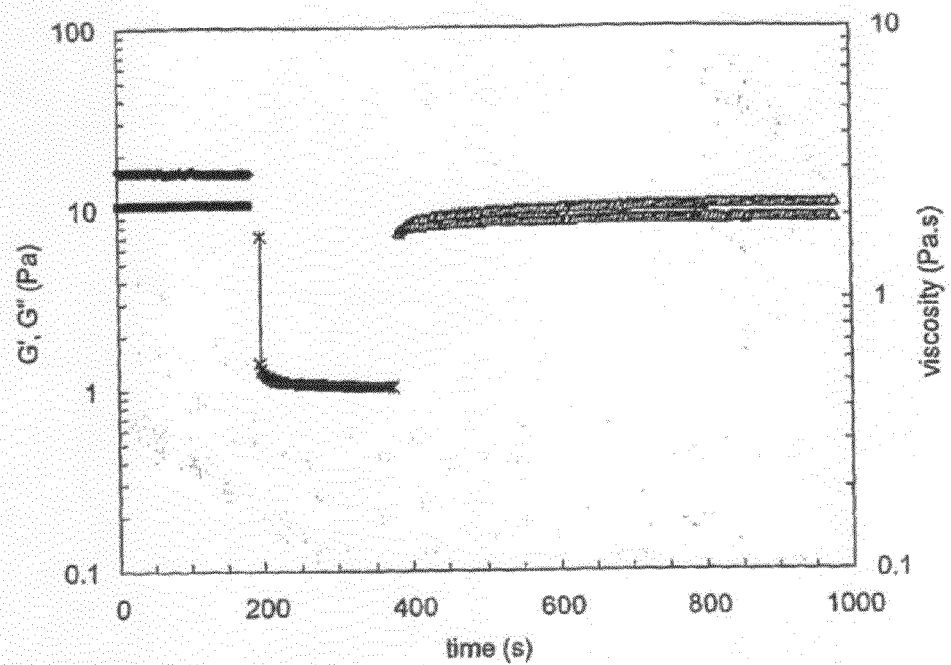
FIGS. 3A-3C show results of compounds described in example 13 during a recovery test.
Figure 3B:
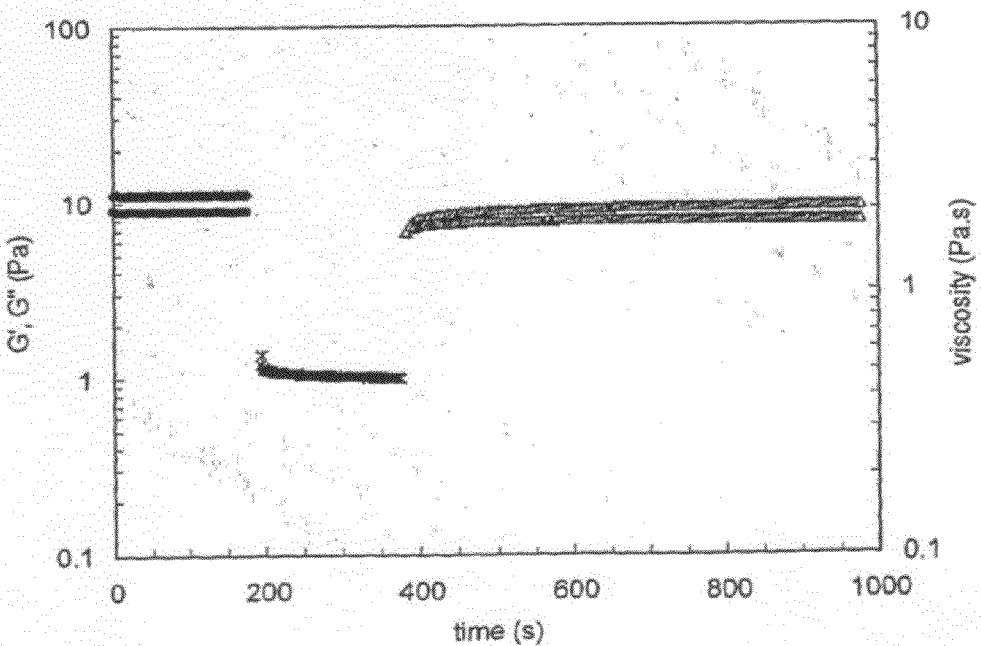
Figure 3C:
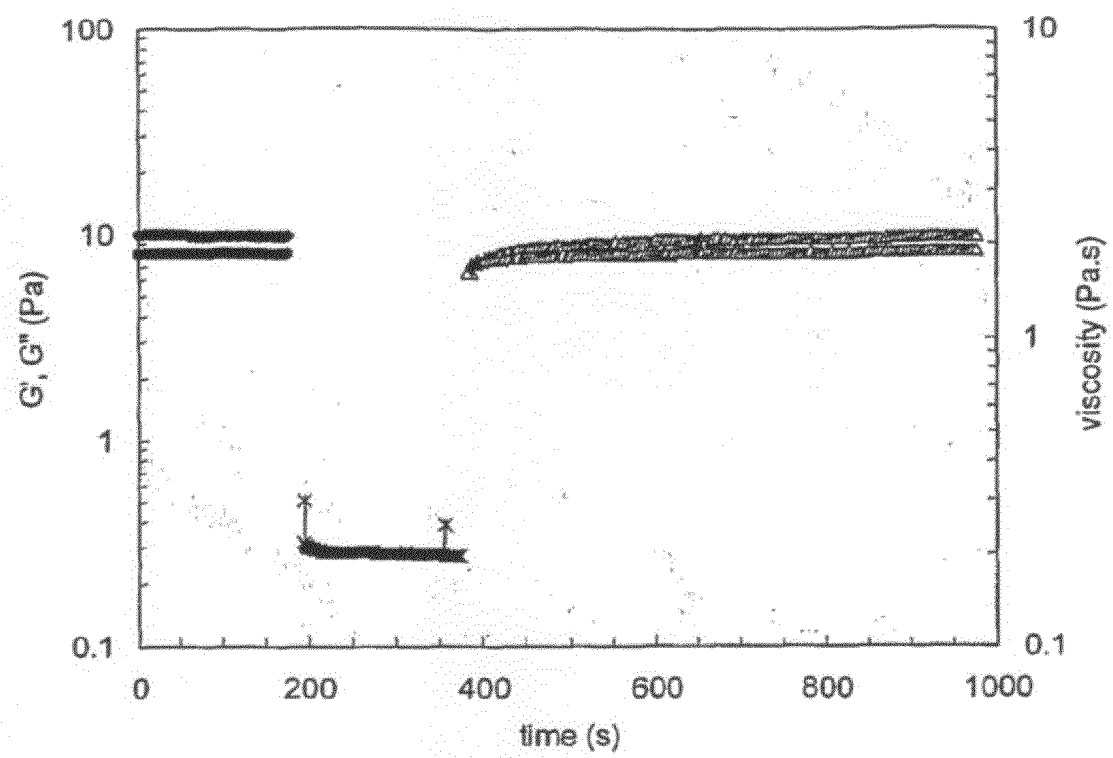

The behaviour of compounds described in example 13 is shown during a recovery test in FIGS. 3a, 3b, 3c: it is possible to observe a complete recovery of both elastic and viscous components in each step.

Conclusions

These studies proved that some representative derivatives according to the invention, submitted to rheological characterization, exhibit different viscoelastic behaviours depending on cross-linking degree, ranging from a viscous solution to a strong gel-like behaviour. Furthermore, it was demonstrated the high capacity in recovering viscoelastic properties after a complete rheological working schedule applied.

All experimental results confirm the great flexibility and reproducibility of the process of the invention for the synthesis of the claimed compounds.

The results of the rheological characterisation of some samples representative of the products obtained are set out in Table 1.

| Example no. | Shear viscosity $\eta 0$ [Pa·s] | Shear viscosity $\eta$at shear rate 700 s−1 [Pa·s] | Storage modules G' at 1 Hz [Pa] | Loss modules G" at 1 Hz [Pa] | D.S. ester | D.S. Links |
|---|---|---|---|---|---|---|
| linear native | 0.1 | 0.05 | np | np | 0 | 0 |
| linear butyrate ester | 0.008 | 0.007 | np | np | 0.07 | 0 |
| 4 | 10.000, 0 | 0.09 | 60 | 21 | 0.12 | 0.03 |
| 5 | 0.9 | 0.05 | 0.8 | 1.8 | 0.05 | 0.01 |
| 6 | 8.000, 0 | 0.2 | 32 | 12 | 0.08 | 0.03 |
| 10 | 87.000, 0 | 0.10 | 165 | 38 | 0.15 | 0.05 |
| 13 | 30.0 | 0.07 | 3.1 | 3.3 | 0.06 | 0.02 |
| 14 | 0.06 | 0.01 | np | np | 0.06 | 0.01 |
| 15(1) | 180.000, 0 | 15 | 777.3 | 173.8 | 0.06 | 0.01 |

(1)The gel was swollen in a 0.9% NaCl at pH = 5.5 water solution; the polymer concentration was 2% w/w.

(1) The gel was swollen in a 0.9% NaCl at pH=5.5 water solution; the polymer concentration was 2% w/w.

The invention claimed is:

1. Acid autocrosslinked polysaccharides, characterised by the concomitant presence of esters with formic and with non-polysaccharide carboxylic acids and auto-cross-linked by esters between the acid groups of the same polysaccharide and the alcoholic groups of the repetitive units, wherein the starting polysaccharide is a glycosaminoglycan selected from hyaluronan, chondroitin sulphate, heparan sulphate, dermatan sulphate, and keratan sulphate and wherein the esters of the non-polysaccharide carboxylic acids on the hydroxyls present a degree of substitution ranging between 0.01 and 0.9×N, where N is the number of hydroxyls present in the repetitive unit, and the formic ester is present in the range between 0.01 and 0.2.

2. The acid autocrosslinked polysaccharides as claimed in claim 1, wherein the carboxyl functions are present in acid or salified form.

3. The acid autocrosslinked polysaccharides as claimed in claim 1, having a molecular weight selected between $10^3$ and $10^7$ Daltons.

4. The acid autocrosslinked polysaccharides as claimed in claim 1, in which the non-polysaccharide carboxylic acid is chosen from the group of acetic, propionic, butyric, isobutyric, valeric, isovaleric and crotonic acid.

5. The acid autocrosslinked polysaccharides as claimed in claim 1, wherein the esters of the non-polysaccharide carboxylic acids on the hydroxyls present a degree of substitution ranging between 0.01 and 0.5 in relation to the repetitive unit.

6. A process for the preparation of the acid autocrosslinked polysaccharides as described in claim 1, which comprises the following steps:
   a) solubilisation of the carboxylated polysaccharide in formamide by heating;
   b) addition of an anhydride of the non-polysaccharide acid at room temperature for a time comprised between 10 minutes and 2 hours;
   c) addition of a base and allow to react at room temperature for a period between 4 hours and 24 hours;
   d) addition of a water solution of sodium chloride and neutralisation to a pH between 6 and 7.5;
   e) purification of the reaction mixture by means of dialyses; and
   f) recovery of the polymer by means of lyofilization.

7. The process as claimed in claim 6, wherein the anhydride is the anhydride chosen from the acetic, propionic, butyric, isobutyric, valeric, isovaleric and crotonic.

8. The process as claimed in claim 6, wherein the base is chosen from an organic base containing an atom of trisubstituted nitrogen, an inorganic base and a salt of an organic acid with sodium and potassium.

9. The process for the preparation of the acid autocrosslinked polysaccharides as described in claim 6, wherein the formate ester is formed from the hydrolysis of formamide in the presence of one of the anhydrides selected from acetic, propionic, butyric, isobutyric, valeric, isovaleric and crotonic and one of the bases chosen from an organic base containing an atom of trisubstituted nitrogen, an inorganic base and a salt of an organic acid with sodium and potassium.

10. A medical device comprising the acid polysaccharides as claimed in claim 1.

11. The acid autocrosslinked polysaccharides as claimed in claim 2, wherein the carboxyl functions are salified with alkaline metals.

12. The acid autocrosslinked polysaccharides as claimed in claim 2, wherein the carboxyl functions are salified with sodium.

13. The process of claim 8 wherein the inorganic base is sodium or potassium salt of phosphoric acid.

14. The process of claim 8 wherein the salt of an organic acid is potassium or sodium acetate.

15. The medical device of claim 10 wherein said medical device is selected from the group comprising moisturizing agents, intra-articular viscosupplementation agents, anti-tissue adherence filling materials in surgery, and materials for covering wounds and sores.

* * * * *